United States Patent

Basaj et al.

Patent Number: 5,848,983
Date of Patent: *Dec. 15, 1998

[54] JOINT FLEXION AND EXTENSION AND EXTENSION SPLINTS

[75] Inventors: Barbara L. Basaj; Carl E. Krippendorf, both of Milwaukee, Wis.

[73] Assignee: Smith & Nephew, Inc., Memphis, Tenn.

[*] Notice: The term of this patent shall not extend beyond the expiration date of Pat. No. 5,681,269.

[21] Appl. No.: 852,984

[22] Filed: May 8, 1997

Related U.S. Application Data

[63] Continuation-in-part of Ser. No. 572,207, Dec. 13, 1995, Pat. No. 5,681,269.

[51] Int. Cl.⁶ ..................................................... A61F 5/00
[52] U.S. Cl. ................................... 602/22; 602/5; 602/21
[58] Field of Search ........................... 602/5–7, 20–22; 128/877–880

[56] References Cited

U.S. PATENT DOCUMENTS

| | | | |
|---|---|---|---|
| 4,441,489 | 4/1984 | Evans et al. | 602/22 |
| 4,829,988 | 5/1989 | Caminiti | 602/22 |
| 5,191,903 | 3/1993 | Donohue | 602/21 X |
| 5,328,448 | 7/1994 | Gray, Sr. | 602/22 |
| 5,376,091 | 12/1994 | Hotchkiss et al. | 602/22 X |
| 5,681,269 | 10/1997 | Basaj et al. | 602/21 X |

FOREIGN PATENT DOCUMENTS

| | | | |
|---|---|---|---|
| 940734 | 12/1948 | France | 602/20 |
| 93293 | 8/1897 | Germany | 602/5 |
| 191678 | 11/1907 | Germany | 602/5 |

*Primary Examiner*—Richard J. Apley
*Assistant Examiner*—Denise Pothier
*Attorney, Agent, or Firm*—Pravel, Hewitt & Kimball

[57] ABSTRACT

An adjustable finger support for the flexion or extension of stiffened interphalangeal joints of a finger of the human hand including an elongated, hinged support base adapted with means for securely, yet comfortably holding the phalanges of the finger in place throughout the course of treatment. The elongated base is divided at hinges into respective support sections for the proximal, middle and distal phalanges of the finger, depending upon which of the DIP and PIP joints of the finger are to be treated. Jacking mean, such as a screw jack in the form of an elongated set screw operates in conjunction with hinged attachments to the respective proximal, middle and distal phalangeal support sections to 1) maintain the set position of the angle of the respective base portions and 2) to provide firm, controllable articulation of the joint over a wide range by selective operation of the jacking means.

25 Claims, 7 Drawing Sheets

JOINT FLEXION AND EXTENSION AND EXTENSION SPLINTS

CROSS REFERENCE TO RELATED APPLICATIONS

This application is a continuation in part of application Ser. No. 08/572,207 filed Dec. 13, 1995, now U.S. Pat. No. 5,681,269.

BACKGROUND OF THE INVENTION

1. Field of the Invention

This invention relates to the medical arts and particularly to splinting devices applicable to the hand to correct dysfunction and/or nonfunction of a finger joint due to injury, surgery, deformity or other affliction. The invention particularly relates to devices for selectively providing extension of a contracted distal and proximal interphalangeal joint or flexion of the extended distal and proximal interphalangeal joint of a finger on a human hand, and particularly for treatment of more severe contracture of the proximal interphalangeal joints.

2. Description of the Prior Art

Finger joints may assume a flexed or an extended, stiffened aspect from a variety of occurrences including injury to muscle, tendon and soft tissue, surgery, aging or disease affecting the tendons and joint capsule structure. Among the prior approaches to effect a straightening of an afflicted finger/joint was the application of a straight splint to the volar, or palm side of the finger, including a strap or cinch placed over the finger at the afflicted joint and tightening of the strap to draw the joint downwardly toward the splint. One version of such a splint included a raised portion at the distal end of the splint so that the joint could be hyperextended slightly past the fully extended plane so that any remaining elasticity of the tendon, when unleashed, would draw the finger back to a straight extension. Such a device is illustrated in U.S. Pat. No. 3,794,019 to Ritland, et al. A disadvantage to this style of splint lies in the concentration of force directly on the top of the afflicted joint and at the proximal and distal ends of the finger causing tissue breakdown and pain attributed to concentration of forces at three concentrated locations.

An alternative approach to splinting a finger joint with a flexion contracture involved tensioning of the finger through an elastic or spring movement, which tended to pull the finger against the contraction. Commonly, as the extension of the finger/joint progressed, the prime mover (spring or elastic band) would approach the extent of its throw and the force applied for extension would diminish. This sort of device would thus become less effective as the objective of the treatment was approached and the complete corrective extension was not accomplished. An illustration of a spring powered splint is illustrated and described in U.S. Pat. No. 4,944,290 issued to Hepburn. While effective in treating minor contraction of a finger joint, this apparatus is ineffective in treating severe joint contractions, particularly those where there is severe contracture of the tendons or joint condition causing the contracture to require substantial force to effect the straightening.

A further device for correcting flexion contractures of the proximal interphalangeal joint of a finger is disclosed in U.S. Pat. No. 5,324,251 to Watson. The title of the patented invention is Device for Flexing or Straightening a Joint, however other than a single reference to placement of one of the pads of the device, no means are illustrated or described for the straightening of a joint. In respect of flexion of finger joints, the device illustrated provides a band for mounting a support plate transcending the width of the hand adjacent the metacarpophalangeal joints to which plate one or more cantilever devices are attached for effecting a flexing (closing) action on the finger(s) including the effected joint(s). As illustrated, the device is effective only for limited flexion of the proximal interphalangeal joint. No means is included for flexion of the distal interphalangeal joint. Likewise, no means is illustrated to ensure phalangeal portions of the finger remain securely in place relative to the device through operative manipulation. The device does not anticipate the present invention since there is no disclosure of particular apparatus for providing coordinated extension and the correction of contraction of individual joints.

A similar flexion device to Walters is illustrated in U.S. Pat. No. 5,328,448 to Gray. The device has a base portion which is disposed over the metarcapal phalanges to be firmly held in place thereon. In one embodiment, the device is effectively clamped to the hand by a second base member cooperating to contain the metacarpal phalanges between the respective base portions. With such a platform, cantilever extensions therefrom interact with the proximal/intermediate phalangeal portions of the finger to effect flexion of that included proximal interphalangeal joint. While cantilever extensions of the device are illustrated in contact with the distal interphalangeal joint, there is no illustration of means for the independent securing of the proximal, intermediate and distal phalanges of the finger such that selective flexion of the proximal and distal interphalangeal joints may be accomplished.

A Dynamic Finger Support, subject of U.S. Pat. No. 5,376,091 to Hotchkiss, et al illustrates a flexion/extension joint support having proximal and distal support sections and means for rigidly connecting each support section to the bone of the phalanges. Hinges connecting the support sections are driven by gear mechanisms to effect the flexion or extension of an included joint. Alternative embodiments of the illustrated device have a clutch associated with the gear mechanism for disconnecting it and distraction apparatus for movement of the phalanges our of contact with the associated joint. The apparatus is connected to the phalanges by pins surgically implanted into the bone.

U.S. Pat. No. 5,183,458 issued to Marx illustrates a finger support useful in straightening finger joints, and particularly the proximal interphalangeal joint. The disclosed device is formed of a malleable base having strap means disposed adjacent one end of the base for holding the afflicted finger against the base. At the other end of the base, beyond the joint to be treated, the underside of the base is adapted with an angular support having disposed therein a set screw operable to vary the angle of a bend introduced into the base when the support is applied by the health care professional. The set screw is selectively turned during the course of treatment so that the finger may be incrementally brought to the extended position by means of the set screw driving the angled base back to the flat condition. As may be appreciated by examining the structure of the illustrated support, the device is capable only of treating limited degrees of contracture as well as those only requiring nominal applications of a sustained force for extension. As distinctly pointed out in other portions of this specification, the present invention is directed to providing an extension splint capable of treading a wide range of interphalangeal joint contractions, and particularly those having a higher degree of contracture and those requiring greater than normal forces to accomplish extension or flexion.

SUMMARY OF THE INVENTION

In accordance with the invention claimed herein, there is disclosed an adjustable finger support for the proximal and distal interphalangeal joints of a finger of the human hand wherein an elongated, hinged support base is adapted with means for securely, yet comfortably holding the finger in place throughout the course of treatment. The elongated base is divided at a hinge into respective support sections for the proximal phalanx portion of the finger and the middle phalanx portion of the finger. Jacking mean, such as a screw jack in the form of an elongated set screw operates in conjunction with hinged attachments to the respective undersides of the proximal and middle interphalangeal support sections to 1) maintain the set position of the angle of the respective base portions and 2) to provide firm, controllable articulation of the joint over a wide range by selective operation of the jacking means. Use of set screws as the screw jack permits interchanging of screws of different lengths and the selection of particular operative lengths corresponding to the degree of flexion or extension achieved.

In preferred embodiments of the invention, the adjustable support includes strap holding means on one or more of the support sections so that each of the proximal and middle interphalangeal finger portions may be securely and comfortably secured to the adjustable support.

Further alternative embodiments of the invention include forming the elongated base of a thermoplastic and adaptation of the base at the location of the hinge by scoring or otherwise partially weakening the base material to form an integral hinge. In a preferred embodiment, the scoring includes removal of a portion of the base material in the central section of the base whereby a slot is formed in the base adjacent the joint to be treated permitting the finger joint to intrude into the hinge region and to be treated through a greater range of extension.

Other embodiments of the invention include the formation of the adjustable support of a low temperature thermoplastic material. Such adaption enables the health care professional applying the treatment to the afflicted finger to effectively customize the finger support by making minor adjustments to the form of the respective support sections for more comfortable, secure holding of the finger in the support.

Further objects and advantages of the invention will become apparent from the following description of the preferred and alternative embodiments of the invention.

BRIEF DESCRIPTION OF THE DRAWINGS

The present invention may be more fully understood with reference to the accompanying drawings in which.

DESCRIPTION OF THE PREFERRED EMBODIMENTS

Figure 1:
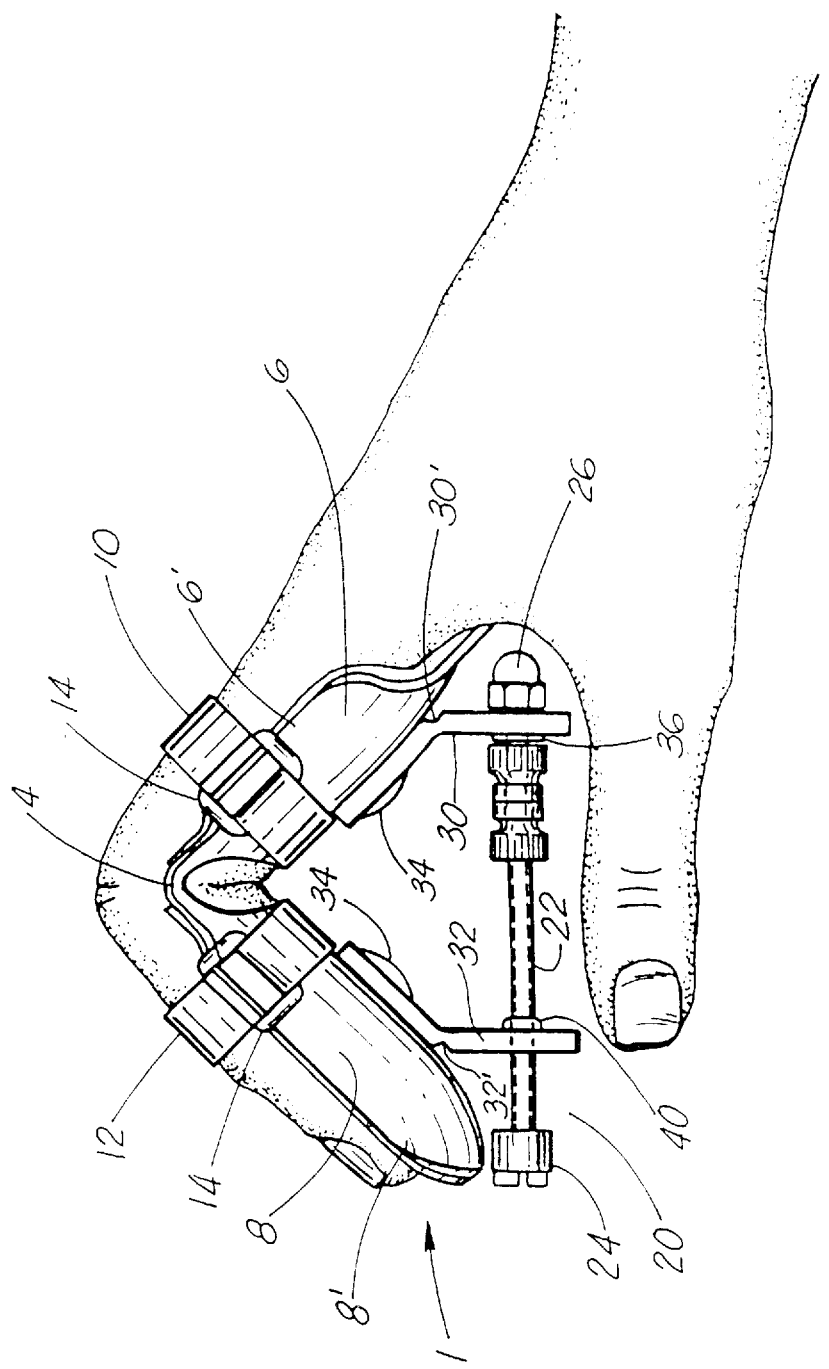
FIG. 1 is a side perspective view of the adjustable finger support, illustrating a finger disposed therein, for use in treatment of contractures of the interphalangeal finger joint.
Figure 2:
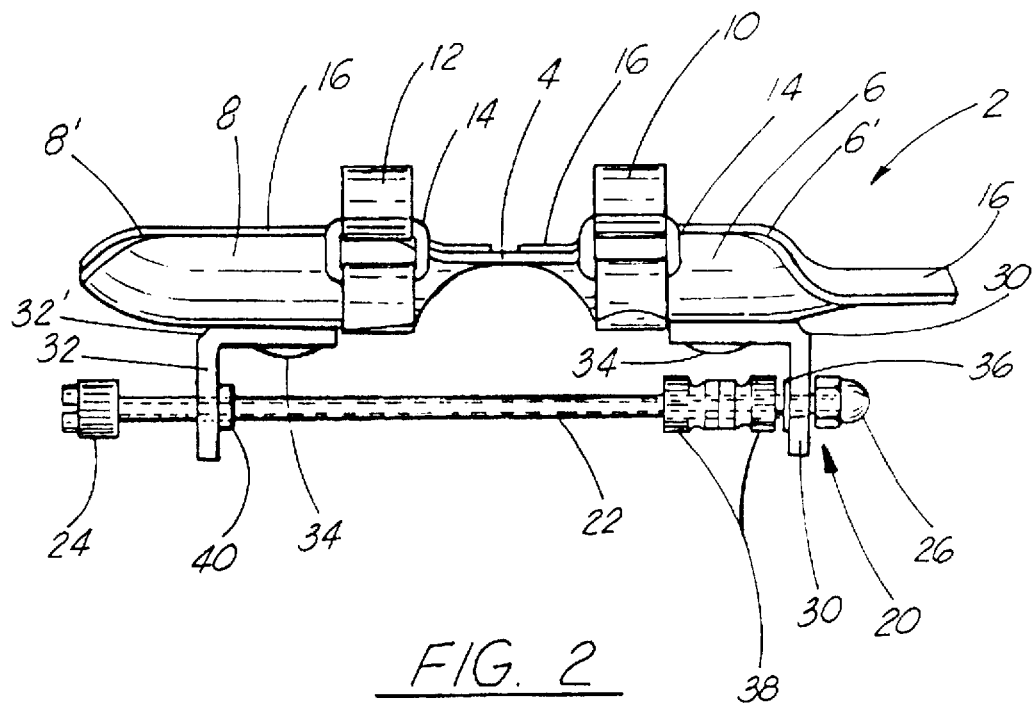
FIG. 2 is a side elevational view of the finger support of FIG. 1.
Figure 4:
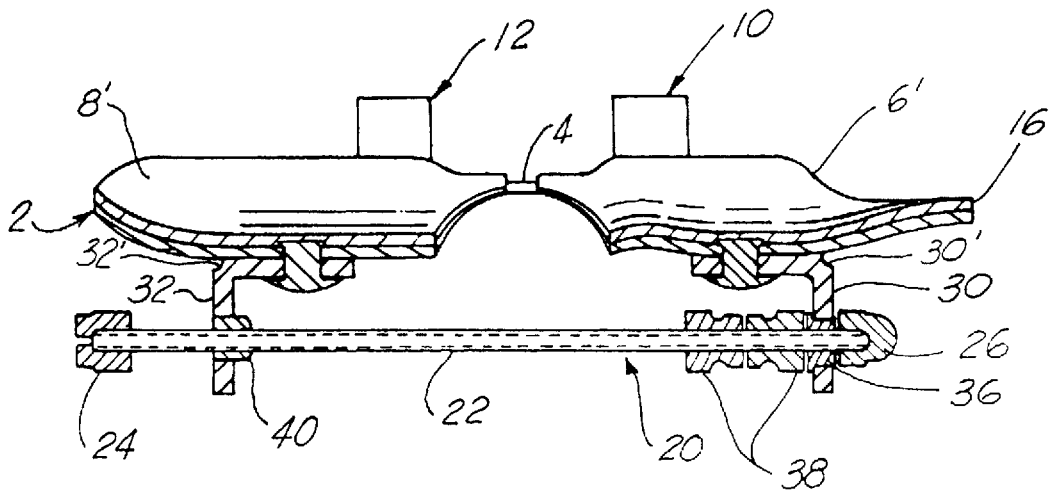
FIG. 4 is a side sectional view taken along line IV—IV of the finger support illustrated in FIG. 3.
Figure 3:
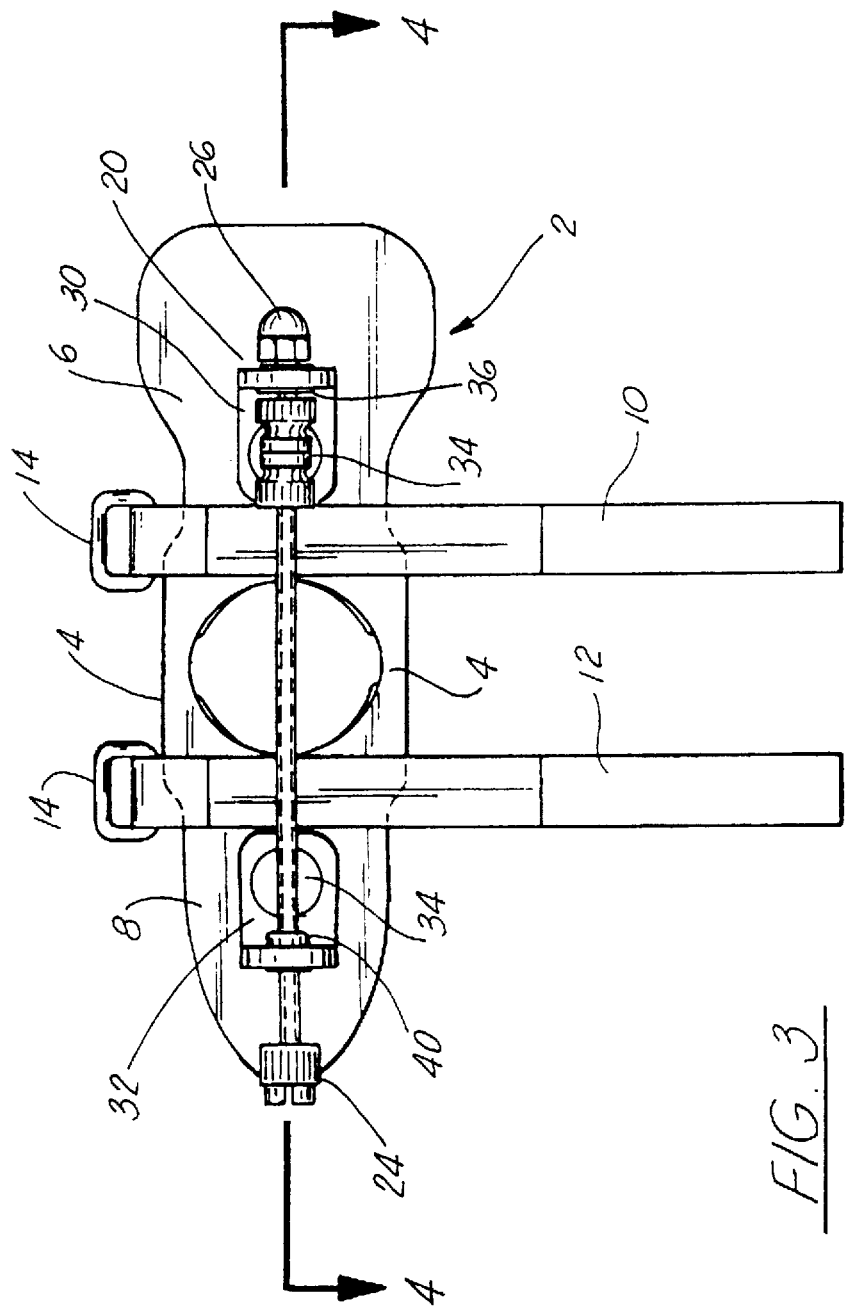
FIG. 3 is a bottom view of the finger support of FIG. 1.

Referring now to the drawings, and in FIGS. 1–3 in particular, the present invention is illustrated in one of the preferred embodiments. The adjustable finger support 1 for treatment of contracted interphalangeal joints of the fingers includes an elongated base 2 having hinge means 4 disposed intermediate base support sections 6 and 8 for the proximal phalanx of the finger and the middle phalanx of the finger, respectively. A further preferred embodiment of the invention includes the middle phalangeal portion 8 extended so as to also accommodate the distal phalanx of the finger. By such extension of phalangeal portion 8, the supporting forces are spread over a wider area thereby distributing the forces applied to the tendons, tissues and joint structure lessening the likelihood of tissue bread-down or discomfort. Disposed on each of the proximal and middle support sections are holding means such as straps 10 (proximal section) and 12 (middle section) for holding the afflicted finger firmly, yet comfortably in the adjustable support 1.

In the illustrated embodiment holding straps 10 and 12 are illustrated on each of the support portions 6 and 8 since this is preferred. It is considered essential to the invention that only the proximal holding means 6 is essential for effective treatment of an afflicted proximal interphalangeal joint. Holding straps 10 and 12 have "D-rings" 14 disposed at one of their respective ends, to enable quick and secure selective fastening of holding straps 10 and 12 about the afflicted finger, enabling effective treatment for the contracture. Those skilled in the art will recognize that such alternatives as hook and loop fasteners (one type of such is sold under the familiar trademark VELCRO), snap means or hook and eye configurations might also be utilized. In the present embodiment, holding straps 10 and 12 are, as a matter of convenience, retained on their respective phalangeal portions 6 and 8 through the use of an adhesive which may be disposed on either or both of the operative interfaces of holding straps 10 and 12 with phalangeal portions 6 and 8. Suitable alternatives will be recognized by those skilled in the art as including rivet means, hook and loop fastening and similar attachment means.

Each of the proximal and middle portions 6 and 8 preferably include upwardly curved sides, 6' and 8' respectively, to aid in retaining the afflicted finger comfortably and securely in the elongated base 2 for the sequential extension of the proximal interphalangeal joint. It should be recognized that, in the instances of severely contracted joints (up to and including 90° of flexion) substantial forces may be imposed in the extension treatment and retaining the afflicted finger in proper position within the adjustable support 1 is accomplished more effectively and comfortably by supporting the proximal and middle phalanges of the finger over as broad an area as is feasible. Further aiding the distribution of the treatment load in the adjustable support 1 is achieved by the inclusion of padding 16 disposed on the interface of the elongated base 2 interacting with the finger. Those skilled in the art will recognize that adhesive backed foam material, flannel-like material and the like may be conveniently affixed to the phalangeal portions 6 and 8.

Operation of the adjustable support 1 in extension is accomplished through jacking means 20, which in the preferred embodiment includes and elongated set screw 22 having a knurled nut 24 disposed at one of set screw 22 for rotation thereof and a cap nut 26 disposed at the opposite end of set screw 22, conveniently providing a stop for jacking means 20. Jacking means 20 is disposed on elongated base 2 so as to provide articulation of proximal phalangeal portions 6 and 8 about hinge means 4 through jack hinges 30 and 32. Jack hinges 30 and 32 are attached to phalangeal portions 6 and 8 of base 2 by means 34 such as rivets, or other suitable fastening means as is known in the art. In the illustrated embodiment, jack hinge 30 has an eyelet journal 36 disposed therein through which set screw 22 is rotatably mounted. Set screw 22 is maintained in longitudinal relative position at jack hinge 30 through the interaction of cap nut 26 and blocking nuts 38 which are set in relative lateral position so that set screw is retained for free movement rotational in eyelet 36 however, is restrained against lateral movement relative to eyelet 36 and hinge 30 only as is required to permit the rotational movement. Those skilled in the art will recognize that alternative means for the mounting of jacking means 20 in jack hinge 30 might be utilized. The illustrated embodiment is particularly useful in that the use of a cap nut 26 and blocking nuts 38 allow for the quick disassembly of the jack means and the utilization of differently sized (lengths) set screws 22 as are convenient for articulation of the adjustable support 1 throughout its broad operable range.

Set screw 22 is disposed in jack hinge 32 by means of a jack nut 40 secured against rotation in jack hinge 32. Jack nut 40 is chosen to have a cooperating bore and internal thread to cooperate with the thread on set screw 22 during rotation of set screw 22. In conventional practice, clockwise rotation of knurled nut 24 will draw jack hinge 32 away from jack hinge 30 causing phalangeal portions 6 and 8 to articulate about hinge means 4. In the usual operation of the adjustable support 1, phalangeal portions 6 and 8 will be articulated to an angle to approximately match the contracture of the afflicted finger such that the adjustable support 1 may be applied to the finger in its contracted condition. Thereafter, in order to articulate a stiffened, flexed joint, set screw 22 is rotated by the health care professional to extend, or move phalangeal portions into and through an obtuse angle toward full extension of the finger. Effecting the treatment will likely be done in successive, sequential rotations of set screw 22, providing incremental, step-wise extension of the finger in amounts tolerable by the patient, and according to the professional judgement of the health care professional. In preferred embodiments of the invention, adjustable support 1 is supplied with a plurality of set screws, of varying lengths. Set screw lengths of 2, 3, 4 and 5 inches provide a range of screw lengths for the user to optionally interchange screws 22 selecting one which best accommodates the current degree of flexion. By the selection of such a suitable size, excessive overhang of set screw 22 beyond hinge 32 is avoided thereby reducing the probability that the screw may snag on a foreign object.

Particular advantage is achieved in the present invention by fabricating elongated base of a low temperature thermoplastic material. Low temperature thermoplastic materials are those which soften under heat and are capable of being molded and shaped with hand pressure, and subsequently harden retaining the molded shape on cooling without undergoing chemical changes. A low temperature material, suitable for use as an adjustable splint should soften at sufficiently low temperatures so as to allow for molding directly on the patient without injury due to scalding or burning of the skin. Suitable polymers which melt or soften at temperatures ranging from 50° C. to 100° C. include poly (ethyleneadipate), poly (epsilon-caprolactone), polyvinyl stearate, cellulose acetate, butyrate and ethyl cellulose poly (propylene oxide) containing co-monomers, trans polyisoprene and cis polyisoprene based thermoplastic materials, and polycaprolactone based materials including commercially available polycaprolactone thermoplastic materials known as AQUAPLAST, SYNERGY, EZEFORM, POLYFORM and POLYFLEX II. These thermoplastic materials are available from the Rehabilitation Division of Smith & Nephew Inc., N104, W13400 Donges Bay Road, Germantown Wis. 53022.

A thermoplastic adjustable splint 1 can be made according to the method claimed in U.S. Pat. No. 4,240,415, incorporated herein by reference. This patent describes a thermoplastic material formed from a thermoplastic polyester having a melting point between about 50° C. and 100° C., and more particularly a poly (epsilon-caprolactone) having a weight average molecular weight of over 5,000 with a half time crystallization at 36° C. of between 0.5 and 10 minutes. At room temperature the poly (epsilon-caprolactone) is quite stiff with a 1% secant modulus of 50,000 psi at 23° C. The stiffness remains high as the temperature is increased. At 60° C. some melting occurs and the stiffness modulus is 20,000 psi. Additionally, some of the poly (epsilon-caprolactone) mixtures become transparent when heated which is useful when molding and placing a splinting device on a limb such as a finger. The thermoplastic material also has 100% elastic memory which allows it to be reheated and reshaped repeatedly.

In a preferred embodiment for treating a contracted interphalangeal joint, the thermoplastic material is precut in a shape that conforms to the illustrations in FIGS. 1–3. The thermoplastic material is conveniently formed with the upstanding curved edges 6' and 8' illustrated at FIGS. 1 and 2. The thermoplastic material also facilitates the formation of a particularly useful hinge means 4 and jack hinges 30 and 32. As may be best seen in FIG. 3, however also visible in FIGS. 1 and 2, hinge means 4 is integrally located in base 2, being formed by scoring including thinning or removal of a portion of the base material. In the illustrated embodiment, the formation of hinge means 4 is accomplished by scoring the thermoplastic material with a notch or, preferably, removal of an oval of material from the central portion of base 2, leaving an opening intermediate the two sides of the base 2. With the particular material used for forming base 2, the oval is approximately 1 and a quarter inches in major diameter, and the remaining material on the sides of base 2 at the hinge is about one-eighth inches. As is illustrated in FIG. 1, such an integral hinge means 4 provides room for the flexed proximal interphalangeal joint of the finger to intrude into the hinge means and be more comfortably and securely contained within adjustable support 1. Characteristics of the specific thermoplastic material chosen may require adjustment of the dimensions of the hinge means.

As with hinge means 4, the low temperature thermoplastic material selected for base 2, the same material is particularly useful for forming jack hinges 30 and 32. Such jack hinges 30 and 32 are readily formed by precutting a rectangular piece of thermoplastic material, conveniently one half inches by one and a quarter inches and scoring the material along a laterally extending line intermediate their ends to form the hinge joint 30' and 32'. By reducing the material thickness to approximately one-half its original thickness, an effective hinge is formed. The precut, scored material may then be assembled to the respective phalangeal portions 6 and 8 as illustrated in the figures.

Referring now to the alternative embodiment of the present invention wherein a stiffened, extended finger may be treated by controlled, progressive flexion of the stiffened joints, the embodiment is illustrated in FIGS. 5 through 8. The adjustable finger support 51 for treatment of stiffened, extended distal and proximal interphalangeal joints of the fingers (i.e., a DIP-PIP Flexion Splint) includes an elongated base 52 having hinge means 54 disposed intermediate superior supports 56, 57 and 58 for the distal phalanges portion, the middle phalanges, and the proximal phalanges of the finger, respectively. The preferred embodiment of this alternative embodiment of the invention includes the superior supports 56, 57 and 58 extended over substantially all of the phalanges so as to spread the supporting forces over as wide an area as practically possible thereby spreading the forces applied to the joint structure lessening the likelihood of tissue break-down or discomfort. Such practical maximization of superior support sections is limited only by the placement of integral hinges 54 and their included cut outs 55 enabling the knuckles K of the finger at the distal interphalangeal joint (DIP) and the proximal interphalangeal (PIP) joint to protrude into the opening accommodating flexion of the involved joints. Disposed on each of the proximal, middle and distal phalangeal supports are holding means such as straps 60 (proximal section), 61 (middle section) and 62 (distal section) for holding the afflicted finger firmly, yet comfortably in the adjustable support 51.

Figure 5:
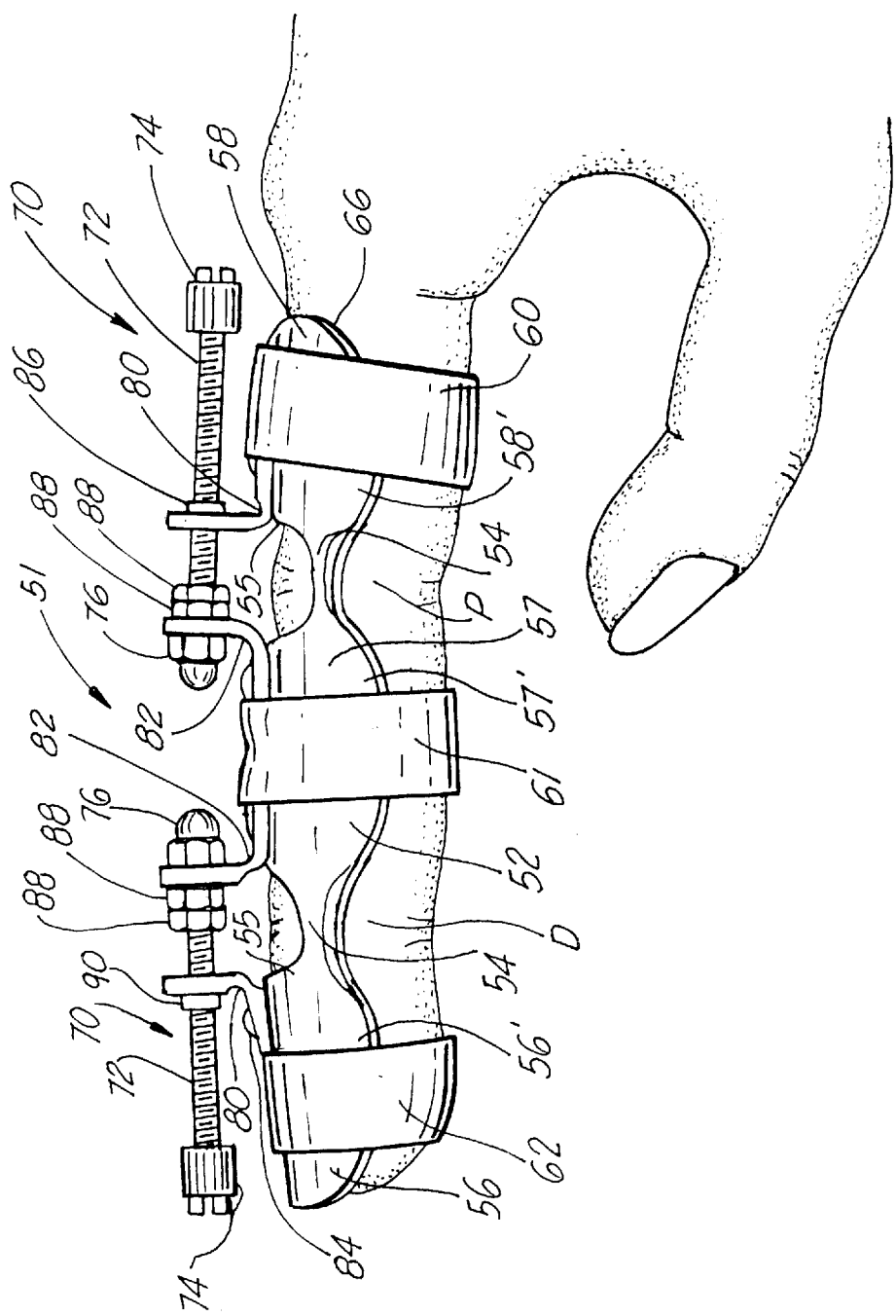
FIG. 5 is a side perspective view of an alternative embodiment of an adjustable finger support, illustrating a finger disposed therein, for use in treatment of an extended, stiffened interphalangeal finger joints.
Figure 6:
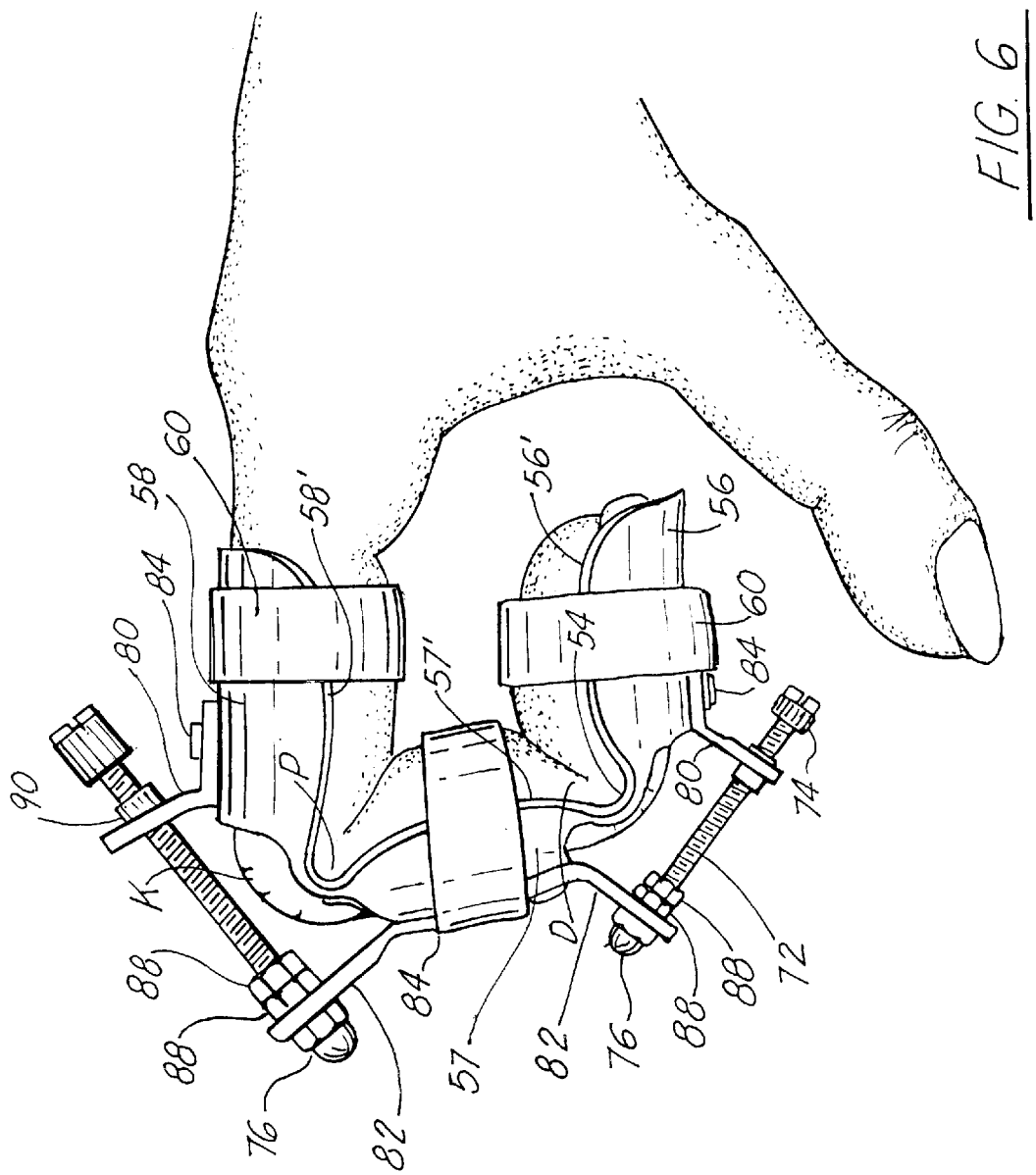
FIG. 6 is a side perspective view of the embodiment illustrated in FIG. 5 wherein the flexion provided by the invention has articulated the interphalangeal joints of the finger.

As with the extension splint embodiment described in FIGS. 1 through 4, hinge 54 is integrally disposed in base 52, being formed by scoring of the material of base 52 such as thinning or removal of a portion of the base material. In the illustrated embodiment, the formation of hinge means 54 is accomplished by scoring the thermoplastic material with a notch or, preferably, removal of an oval of material from the central portions of base 52 corresponding to the locations of the proximal and distal interphalangeal joints, leaving an opening intermediate the two sides of the base 52. With the particular material used for forming base 52, the oval is approximately 1 inch in major diameter, and the remaining material on the sides of base 52 at the hinges is about one-quarter inches. As is illustrated in FIGS. 5 and 6, such an integral hinge means 54 provides room for the flexed proximal and distal interphalangeal joints of the finger to intrude into the hinge means and be more comfortably and securely contained within adjustable support 51. Characteristics of the specific thermoplastic material chosen may require adjustment of the dimensions of the hinge means.

As with hinge means 54, the low temperature thermoplastic material selected for base 52, the same material is particularly useful for forming jack hinges 80 and 82. Such jack hinges 80 and 82 are readily formed by precutting a rectangular piece of thermoplastic material, conveniently one half inches by one and a quarter inches and scoring the material along a laterally extending line intermediate their ends to form the hinge joint 80' and 82'. By reducing the material thickness to approximately one-half its original thickness, an effective hinge is formed. The precut, scored material may then be assembled to the respective phalangeal supports 56, 57 and 58 as illustrated in the figures and discussed previously In the illustrated embodiment holding straps 60, 61 and 62 are illustrated on each of the supports 56, 57 and 58 since this is preferred. It is considered essential to the invention that only the proximal holding means 60 and distal holding means 62 are essential for effective treatment of an afflicted proximal interphalangeal joint. Holding straps 60, 61 and 62 for this alternative embodiment of the invention are illustrated as having hook and loop type fastening surfaces as contrasted with "D-rings" 14 disposed on holding straps 10 and 12 illustrated on the embodiment of the invention illustrated in FIGS. 1 through 4. Hook and loop fastening means disposed on the respective ends of straps 60, 61 and 62 enable quick and secure selective fastening of holding straps 60, 61 and 62 about the afflicted finger, enabling effective flexion treatment for the stiffened, extended joints. Those skilled in the art will recognize that such alternatives to hook and loop fasteners (one type of such is sold under the familiar trademark VELCRO), such as the afore mentioned D-rings, snap means or hook and eye configurations might also be utilized. In the present embodiment, holding straps 60, 61 and 62 are, as a matter of convenience, are retained on their respective phalangeal dorsal supports 56, 57 and 58 through the use of an adhesive which may be disposed on either or both of the operative interfaces of holding straps 60, 61 and 62 with phalangeal support sections 56, 57 and 58. Suitable alternatives will be recognized by those skilled in the art as including rivet means, hook and loop fastening and similar fixed attachment means.

Each of the distal, middle and proximal supports 56, 57 and 58 preferably include downwardly curved sides, 56', 57' and 58' respectively, to aid in retaining the afflicted finger comfortably and securely in the elongated base 52 of splint 51 for the sequential flexion of the proximal and distal interphalangeal joints. It should be recognized that, in the instances of severely stiffened joints, substantial forces may be imposed in the extension treatment and retaining the afflicted finger in proper position within the adjustable support 51 is accomplished more effectively and comfortably by supporting the proximal, middle and distal phalanges of the finger over as broad an area as is feasible. Further distribution of the treatment load in the adjustable support 51 is achieved by the inclusion of padding 66 disposed on the interface of the elongated base 52 interacting with the finger. Those skilled in the art will recognize that adhesive backed foam material, flannel-like material and the like may be conveniently affixed to the phalangeal supports 56, 57 and 58.

Operation of the adjustable flexion splint 51 in flexion is accomplished through jacking means 70, being disposed and operable independently on each of the proximal P and distal D interphalanges joints. In the preferred embodiment disclosed, jacking means 70 includes and elongated jack screw 72 having a knurled nut 74 disposed at one of jack screw 72 for rotation thereof and a cap nut 76 disposed at the opposite end of jack screw 72, conveniently providing a stop for jacking means 70. Jacking means 70 is disposed on elongated base 52 so as to provide articulation of the proximal interphalangeal (PIP) joint by being fixedly attached to proximal phalangeal superior support 58 and middle phalangeal support 57 opposite hinge means 54 through jack hinges 80 and 82. Jack hinges 80 and 82 are attached to proximal phalangeal support 58 and middle phalangeal support 57 of base 52 by means 84 such as rivets, or other suitable fastening means as are known in the art. In the illustrated embodiment, jack hinge 82 has an eyelet journal 86 or sleeve means forming a bearing (not shown in FIGS. 5 and 6) disposed therein through which jack screw 72 is rotatably mounted at its distal end. Jack screw 72 is maintained in relative position at jack hinge 80 through the interaction of cap nut 76 and locking nuts 88 which are set in relative lateral position so that set screw is retained for free movement rotational in eyelet 86 however, is restrained against lateral movement relative to eyelet 86 and hinge 82 only as is required to permit the rotational movement. Those skilled in the art will recognize that alternative means for the mounting of jacking means 70 in jack hinge 82 might be utilized. The illustrated embodiment is particularly useful in that the use of a cap nut 76 and blocking nuts 88 allow for the quick disassembly of the jack means and the utilization of differently sized (lengths) jack screws 72 as are convenient for articulation of the adjustable support 51 throughout its broad operable range.

Jacking means 70 is also disposed on distal phalangeal support 56 and middle phalangeal support 57 operably adjacent hinge means 54 and over distal interphalangeal (DIP) joint D. Jacking means 70 for the DIP joint is otherwise constructed and operated as described in relation to proximal interphalangeal joint P.

Jack screw 72 is disposed in jack hinges 80 adjacent its proximal end and by means of an eyelet journal 90 which is secured against rotation in jack hinge 80. Eyelet journal 90 is chosen to have a cooperating bore and internal thread to cooperate with the thread on jack screw 72 such that during rotation of jack screw 72, it moves longitudinally with respect to hinge 80 and eyelet 90. In conventional practice, clockwise rotation of knurled nut 74 distal interphalangeal joint D (and screw 72) will push jack hinge 82 away from jack hinge 80 causing phalangeal supports 56 and 57 to articulate about hinge means 54. Likewise clockwise rotation of nut 74 of Jack screw 72 adjacent proximal interphalangeal joint P causes jack hinge 80 on phalangeal support 58 to move away from hinge 82 causing angular articulation about hinge 54 at the PIP joint.

In the usual operation of the adjustable support 51 for flexion of stiffened, extended DIP and PIP joints, each of pairs of phalangeal superior supports 56–57 and 57–58 will be articulated to an angle to approximately match the stiffened extension of the afflicted finger such that the flexion adjustment support 51 may be applied to the finger in its stiffened, extended condition. Thereafter, the individual jack screws 72 are rotated by the health care professional to flex, or move, the pairs of phalangeal dorsal supports 56–57 and 57–58 through an obtuse angle toward full flexion of the finger. Effecting the treatment will likely be done in successive, sequential rotations of jack screws 72, providing incremental, step-wise flexion of the respective DIP and PIP finger joints in amounts tolerable by the patient, and according to the professional judgement of the health care professional. In preferred embodiments of the invention, adjustable support 51 is supplied with a plurality of set screws, of varying lengths. Set screw lengths of 2, 3, 4 and 5 inches provide a range of screw lengths for the user to optionally interchange jack screws 72 selecting one which best accommodates the current degree of flexion. By the selection of such a suitable size, excessive overhang of set screw 22 beyond hinges 80 is avoided thereby reducing the probability that the screw may snag on a foreign object.

As with PIP extension splint illustrated in FIGS. 1 through 4, particular advantage is achieved in the flexion embodiment of the present invention by fabricating elongated base 52 of a low temperature thermoplastic material. In a similar manner the thermoplastic material is precut in a shape that conforms to the illustrations in FIGS. 7 and 8. The thermoplastic material is conveniently formed with the upstanding curved edges 56', 57' and 58' illustrated in FIGS. 6 and 7. As with the extension PIP splint embodiment illustrated in FIGS. 1 through 4, the thermoplastic material also facilitates the formation of a particularly useful hinge means 54 and jack hinges 80 and 82.

Figure 7:
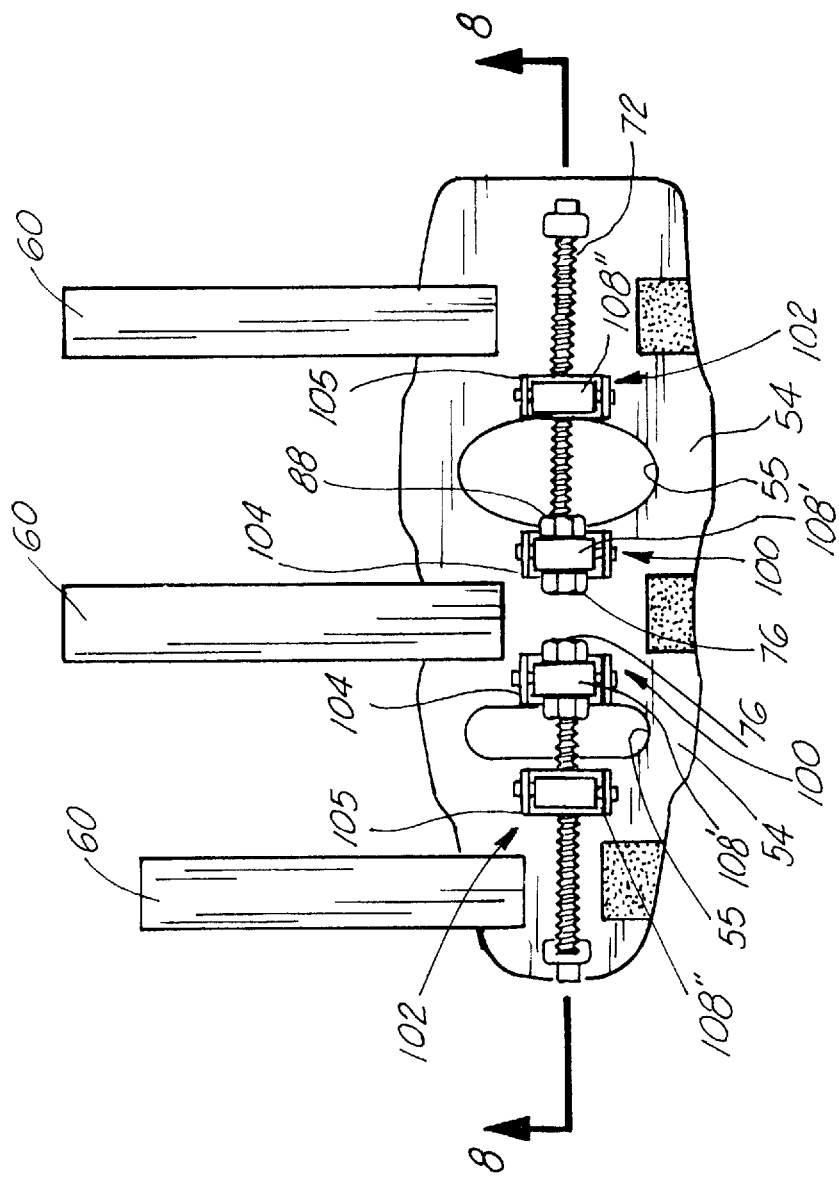
FIG. 7 is a bottom view of the finger support of FIG. 5, shown in plan view without the finger disposed therein.
Figure 8:
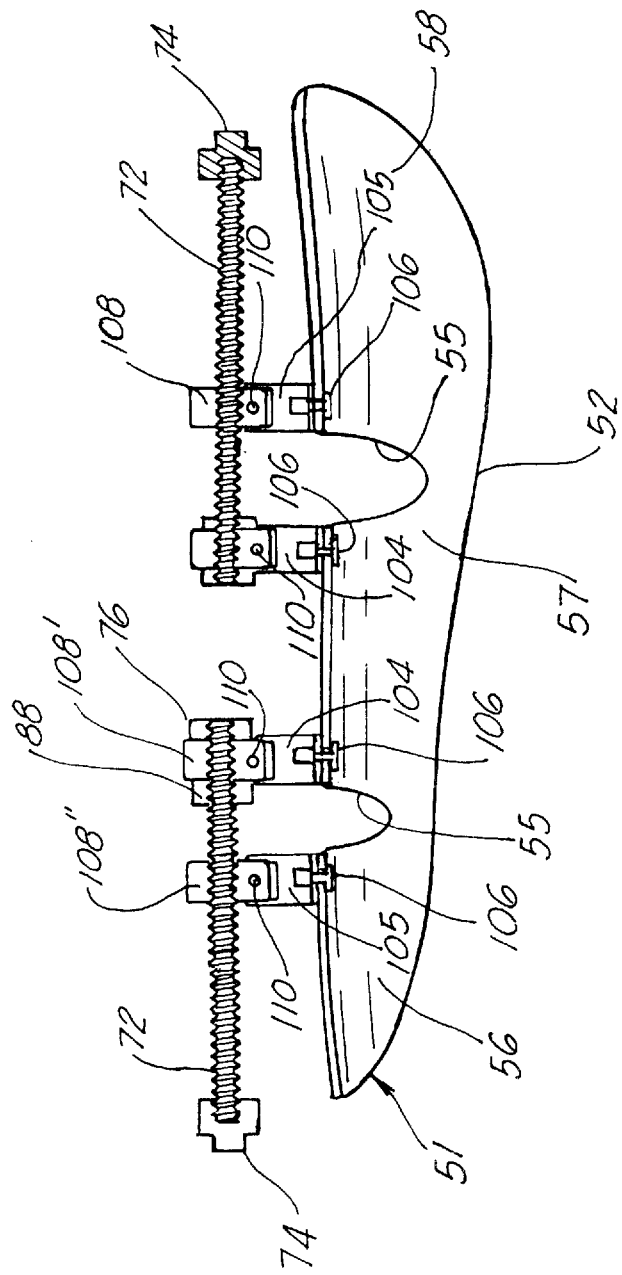
FIG. 8 is a side sectional view taken along line VIII—VIII of the finger support illustrated in FIG. 7.

In an alternative embodiment to jack hinges 80 and 82, FIGS. 7 and 8 illustrate jack hinges 100 and 102 disposed adjacent hinges 54 at each of the DIP and PIP interphalangeal joints. Hinges 100 and 102 include U-shaped base supports 104 and 105, secured to dorsal phalangeal supports 56, 57 and 58 by means such as rivet 106, or other equivalent means for ensuring a firm connection to the respective support section so as to retain the generally upright relationship of base 104 to phalangeal supports 56, 57 and 58 during the transverse loading imposed during the flexion of the DIP and PIP interphalageal joints. As may be further seen in FIGS. 7 and 8, hinges 100 include a sleeve 108 as a bearing for rotary support of jack screws 72, being pivotally mounted in base 104 as by pins on the lateral faces of sleeves 108 cooperating with mounting holes 110 in base 104. Sleeves 108' for jack screws 72 for mounting at their distal ends in bases 104 configured as bearings (e.g., having a smooth interior surface equivalent to eyelet 86 of FIGS. 5 and 6) and jack screws are retained relatively fixed longitudinally by the cooperating action of cap nuts 76 and locking nuts 88. Sleeves 108" for jack screws 72 for mounting at their proximal ends in bases 105 are configured a threaded interior surface (analogous to eyelet journal 90 of FIGS. 5 and 6) such that by rotating the jack screw 72 as by turning knurled nut 74, affects longitudinal movement of jack screw 72 as earlier described.

As will be apparent to persons skilled in the art, various additional modifications, adaptations and variations of the foregoing specifically disclosed embodiments can be made without departing form the objectives and scope of the present invention;

Accordingly, we claim:

1. An adjustable finger support for an interphalangeal joint of a human finger for treating a stiffened condition of said joint comprising:

an elongate base having adjacent phalangeal base portions for supporting the adjacent phalanges of the finger, said elongate base having hinge means disposed intermediate said adjacent phalangeal base portions of said elongate base;

said adjacent phalangeal base portions form an included angle in said elongate base having said hinge means as the apex of said angle;

holding means disposed on at least one of said adjacent phalangeal base portions for releasably holding said phalanges of said finger securely on said phalangeal base portion;

jack means disposed on the side of said elongate base opposite the finger wherein said jack means is pivotally connected by jack hinge means disposed on said adjacent phalangeal base portions whereby operation of said jack means varies the included angle formed by said elongate base having said hinge means as the apex of said angle;

whereby the stiffened finger and joint may be secured in said finger support, wherein said base portions are disposed in angular relationship approximating the angular stiffened condition of said joint between adjacent phalanges of said finger and said support may be thereafter selectively articulated by operation of said jack means causing said base portions to angularly rotate lessening said stiffened condition of said interphalangeal joint.

2. The adjustable finger support according to claim 1 wherein said adjacent phalangeal base portions have lateral edges upturned from said the plane of said base, forming partially convex cross sections for receiving said adjacent phalanges of the finger therein.

3. The adjustable finger support according to claim 1 wherein operation of said jack means rotates said adjacent phalangeal base portions through an obtuse angle.

4. The adjustable finger support according to claim 1 wherein said elongate base is formed of a thermoplastic material.

5. The adjustable finger support according to claim 4 wherein said hinge means is integrally formed in said thermoplastic material by scoring said material.

6. The adjustable finger support according to claim 5 wherein said hinge means is integrally formed in said thermoplastic material by scoring said material to form an oval opening in said thermoplastic material, with the minor axes of said oval aligned substantially parallel to the phalanges.

7. The adjustable finger support according to claim 4 wherein said jack hinge means are formed of a low temperature thermoplastic material.

8. The adjustable finger support according to claim 7 wherein said hinge means in said jack hinge means is formed by scoring said material.

9. The adjustable finger support according to claim 1 wherein said holding means disposed on at least one of said phalangeal base portion includes strap means fixedly attached to said base portions on the side opposite the phalanges.

10. The adjustable finger support according to claim 1 wherein said holding means is disposed additionally on another of said adjacent phalangeal base portions.

11. The adjustable finger support according to claim 1 wherein said jack means is a screw jack operably connected to said elongated base through said jack hinge means.

12. The adjustable finger support according to claim 11 wherein said screw jack is rotatably journaled in first jack hinge means mounted on one of said phalangeal base portions and is secured therein against longitudinal movement relative to said first jack hinge; and said jack means is rotatably journaled in second jack hinge means mounted on an adjacent phalangeal base portion in geared relation whereby rotation of said jack means effects relative longitudinal movement of said second jack hinge means with respect to said jack means.

13. The adjustable finger support according to claim 12 wherein said first jack hinge means includes a U-shaped support fixedly secured to one of said phalangeal base portions adjacent said hinge means of said elongate base and said U-shaped support has pivotally secured therein a bearing for rotatably receiving said jack means; and said second jack hinge means includes a U-shaped support fixedly secured to another of said adjacent phalangeal base portions, adjacent said hinge means of said elongate base and said U-shaped support has pivotally secured therein a sleeve having a screw thread internally of said sleeve complementary to the thread of said screw jack whereby rotation of said screw jack varies the included angle formed by said hinge means in said elongate base.

14. An adjustable finger support for an interphalangeal joint of a human hand for treating a stiffened, extended condition of said joint comprising:

an elongate base having a proximal phalangeal base portion, middle phalangeal base portion and a distal phalangeal base portion for supporting the proximal, middle and distal phalanges of the finger respectively, said elongate base having first hinge means disposed intermediate said proximal phalangeal base portion and said middle phalangeal base portion and having second hinge means disposed intermediate said middle phalangeal base portion and said distal phalangeal base portion of said elongate base;

said proximal phalangeal base portion and said middle phalangeal base portion form a first included angle in said elongate base having said first hinge means as the apex of said angle;

said middle phalangeal base portion and said distal phalangeal base portion form a second included angle in said elongate base having said second hinge means as the apex of said angle;

holding means disposed on at least said proximal phalangeal base portion for releasably holding said proximal phalanges of the finger securely on said proximal phalangeal base portion;

first jack means disposed on the side of said elongate base opposite the finger wherein said jack means is pivotally connected by jack hinge means disposed on said proximal phalangeal base portion and on said middle phalangeal base portion whereby operation of said first jack means varies the included angle formed by said proximal phalangeal base portion and said middle phalangeal base portion of said elongate base having said first hinge means as the apex of said angle;

second jack means disposed on the side of said elongate base opposite the finger wherein said jack means is pivotally connected by jack hinge means disposed on said middle phalangeal base portion and on said distal phalangeal base portion of said elongate base whereby operation of said second jack means varies the included angle formed by said elongate base having said second hinge means as the apex of said angle;

whereby the extended, stiffened finger and joint may be secured in said finger support, wherein said proximal and middle phalangeal base portions and said middle and distal base portions of said elongate base are disposed in angular relationship approximating the angular extension of said joint between said proximal and middle phalanges of the finger and the angular extension of said joint between the middle and distal phalanges of the finger and said support may be thereafter selectively articulated by operation of said first jack means and said second jack means causing, respectively said proximal and middle phalangeal base portions and said middle and distal phalangeal base portions to angularly rotate flexing said stiffened extended condition of the proximal and distal interphalangeal joints.

15. The adjustable finger support according to claim 14 wherein said phalangeal base portions have lateral edges upturned from said the plane of said base, forming partially convex cross sections for receiving the adjacent phalanges of the finger therein.

16. The adjustable finger support according to claim 14 wherein operation of said jack means rotates adjacent phalangeal base portions through an obtuse angle.

17. The adjustable finger support according to claim 14 wherein said elongate base is formed of a thermoplastic material.

18. The adjustable finger support according to claim 17 wherein said hinge means is integrally formed in said thermoplastic material by scoring said material.

19. The adjustable finger support according to claim 18 wherein said hinge means is integrally formed in said thermoplastic material by scoring said material to form an oval opening in said thermoplastic material, with the minor axes of said oval aligned substantially parallel to the phalanges.

20. The adjustable finger support according to claim 17 wherein said jack hinge means are formed of a low temperature thermoplastic material.

21. The adjustable finger support according to claim 20 wherein said hinge means in said jack hinge means is formed by scoring said material.

22. The adjustable finger support according to claim 14 wherein said holding means disposed on said phalangeal base portion includes strap means fixedly attached to said base portion on the side opposite the phalanges.

23. The adjustable finger support according to claim 14 wherein said jack means is a screw jack operably connected to said elongated base through said jack hinge means.

24. The adjustable finger support according to claim 23 wherein said screw jack is rotatably journaled in first jack hinge means mounted on one of said phalangeal base portions and is secured therein against longitudinal movement relative to said first jack hinge; and said jack means is rotatably journaled in second jack hinge means mounted on an adjacent phalangeal base portion in geared relation whereby rotation of said jack means effects relative longitudinal movement of said second jack hinge means with respect to said jack means.

25. The adjustable finger support according to claim 24 wherein said first jack hinge means includes a U-shaped support fixedly secured to said phalangeal base portions adjacent said first hinge means of said elongate base; and said U-shaped support has pivotally secured therein a bearing for rotatably receiving said jack means; and said second jack hinge means includes a U-shaped support fixedly secured to said phalangeal base portions, adjacent said second hinge means of said elongate base and said U-shaped support has pivotally secured therein a sleeve having a screw thread internally of said sleeve complementary to the thread of said screw jack whereby rotation of said screw jack varies the included angle formed by said hinge means in said elongate base.

\* \* \* \* \*